(12) United States Patent
Guracar et al.

(10) Patent No.: US 6,309,357 B1
(45) Date of Patent: Oct. 30, 2001

(54) MEDICAL DIAGNOSTIC ULTRASOUND SYSTEM AND METHOD FOR IMPROVED FLOW OR MOVEMENT DETECTION WITH MULTIPLE CLUTTER FILTERS

(75) Inventors: Ismayil M. Guracar, Redwood City; Patrick J. Phillips, Sunnyvale, both of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/370,758

(22) Filed: Aug. 9, 1999

(51) Int. Cl.[7] ................................................ A61B 08/00
(52) U.S. Cl. ........................................................ 600/454
(58) Field of Search ........................... 600/454, 445, 600/447, 455, 437, 450

(56) References Cited

U.S. PATENT DOCUMENTS

| | | |
|---|---|---|
| 5,152,292 * | 10/1992 | Karp ...................................... 600/454 |
| 5,249,578 | 10/1993 | Karp et al. . |
| 5,349,524 | 9/1994 | Daft et al. . |
| 5,544,659 | 8/1996 | Banjanin . |
| 5,609,155 | 3/1997 | Guracar . |
| 5,664,575 | 9/1997 | Banjanin et al. . |
| 5,709,210 | 1/1998 | Green et al. . |
| 5,846,202 * | 12/1998 | Ramamurthy et al. ............... 600/450 |
| 5,860,930 | 1/1999 | Guracar . |

* cited by examiner

*Primary Examiner*—Marvin M. Lateef
*Assistant Examiner*—Maulin Patel
(74) *Attorney, Agent, or Firm*—Craig A. Summerfield; Brinks Hofer Gilson & Lione

(57) ABSTRACT

A method and system for flow or movement detection is provided. More than one clutter filter is used. Each clutter filter's magnitude versus frequency response is optimized differently. Estimates of the flow or movement are generated from the data output by each of the clutter filters. Using selection or combination of the resulting estimates, the best attributes of each filter are used for imaging.

60 Claims, 5 Drawing Sheets

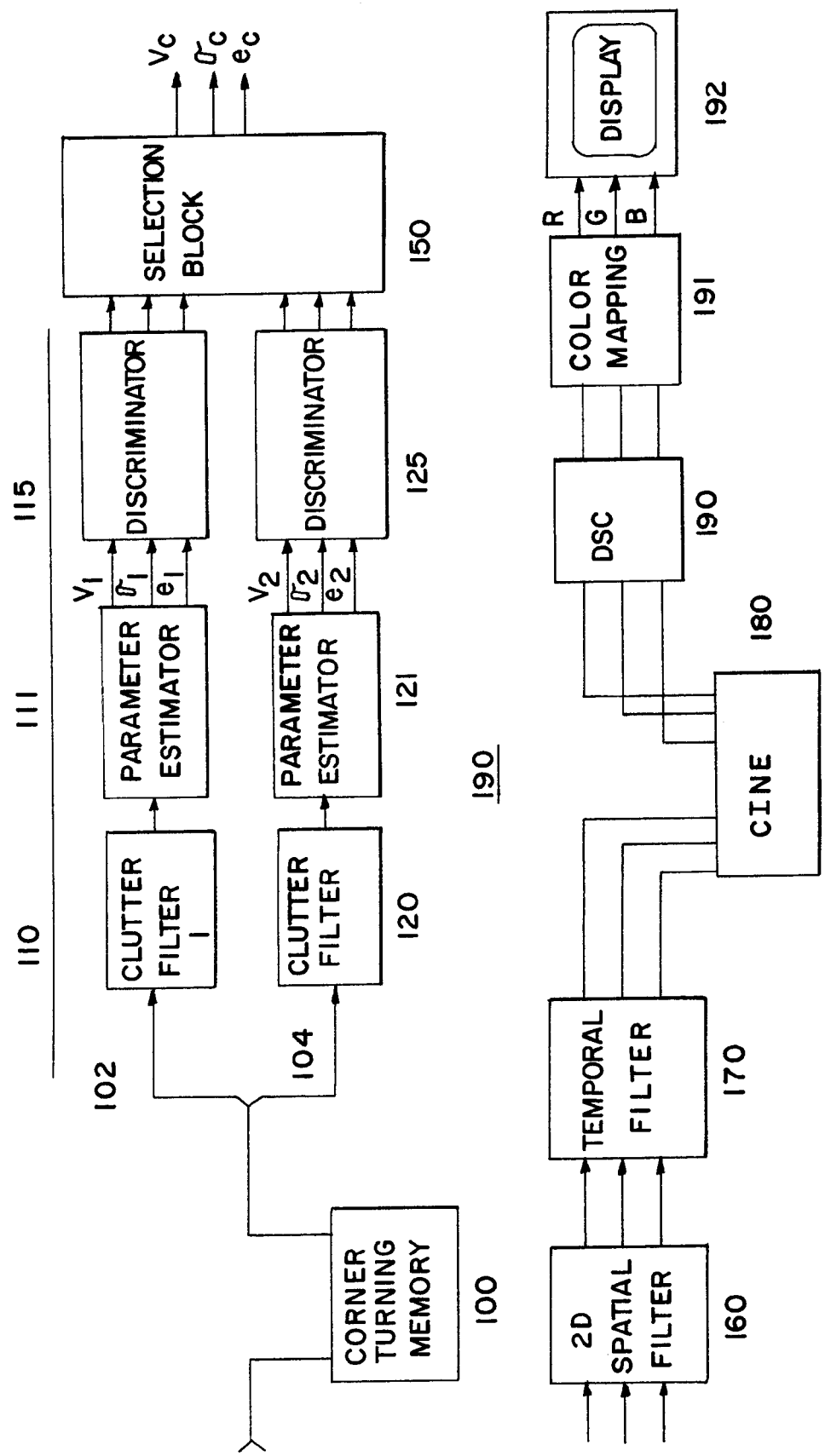

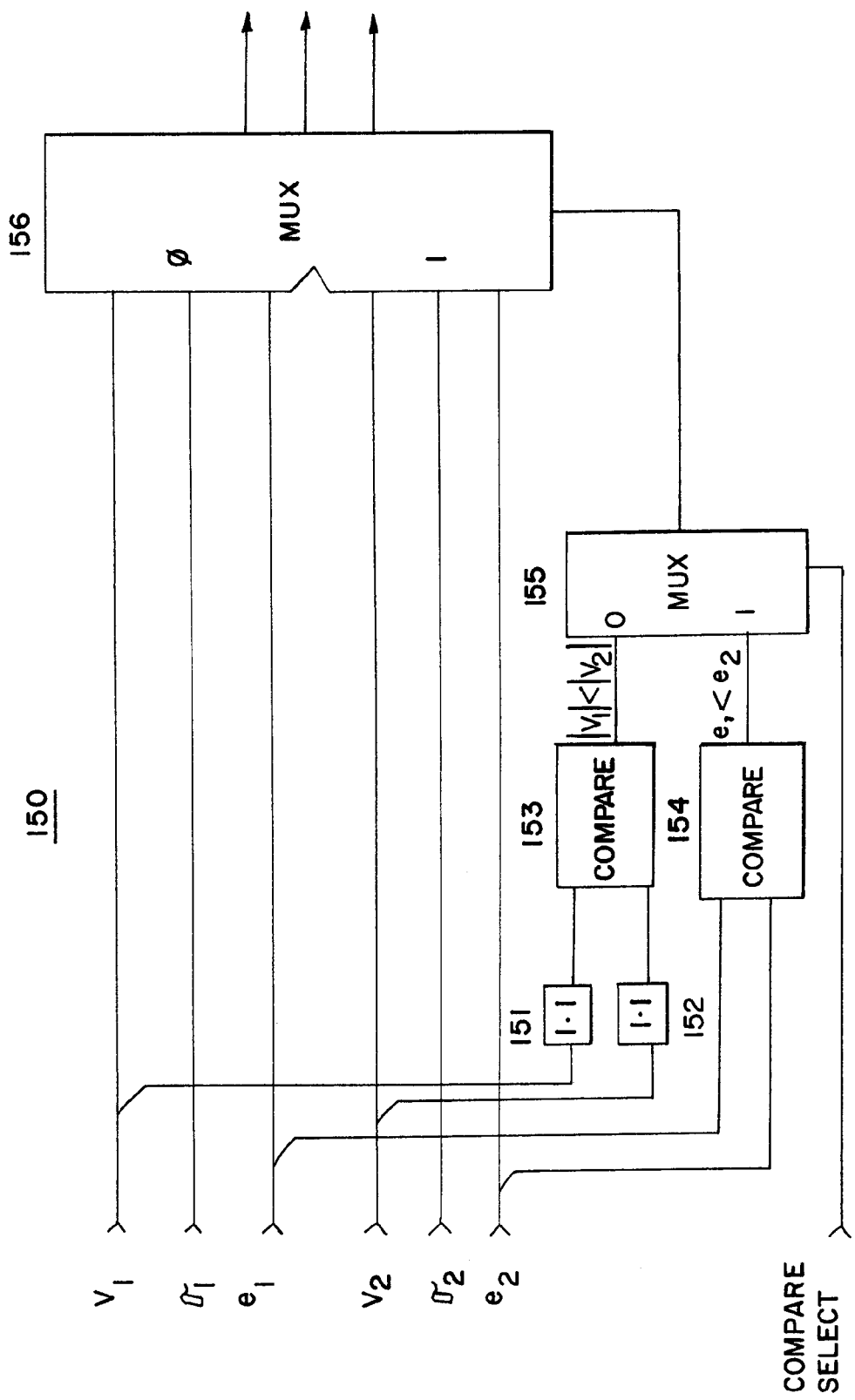

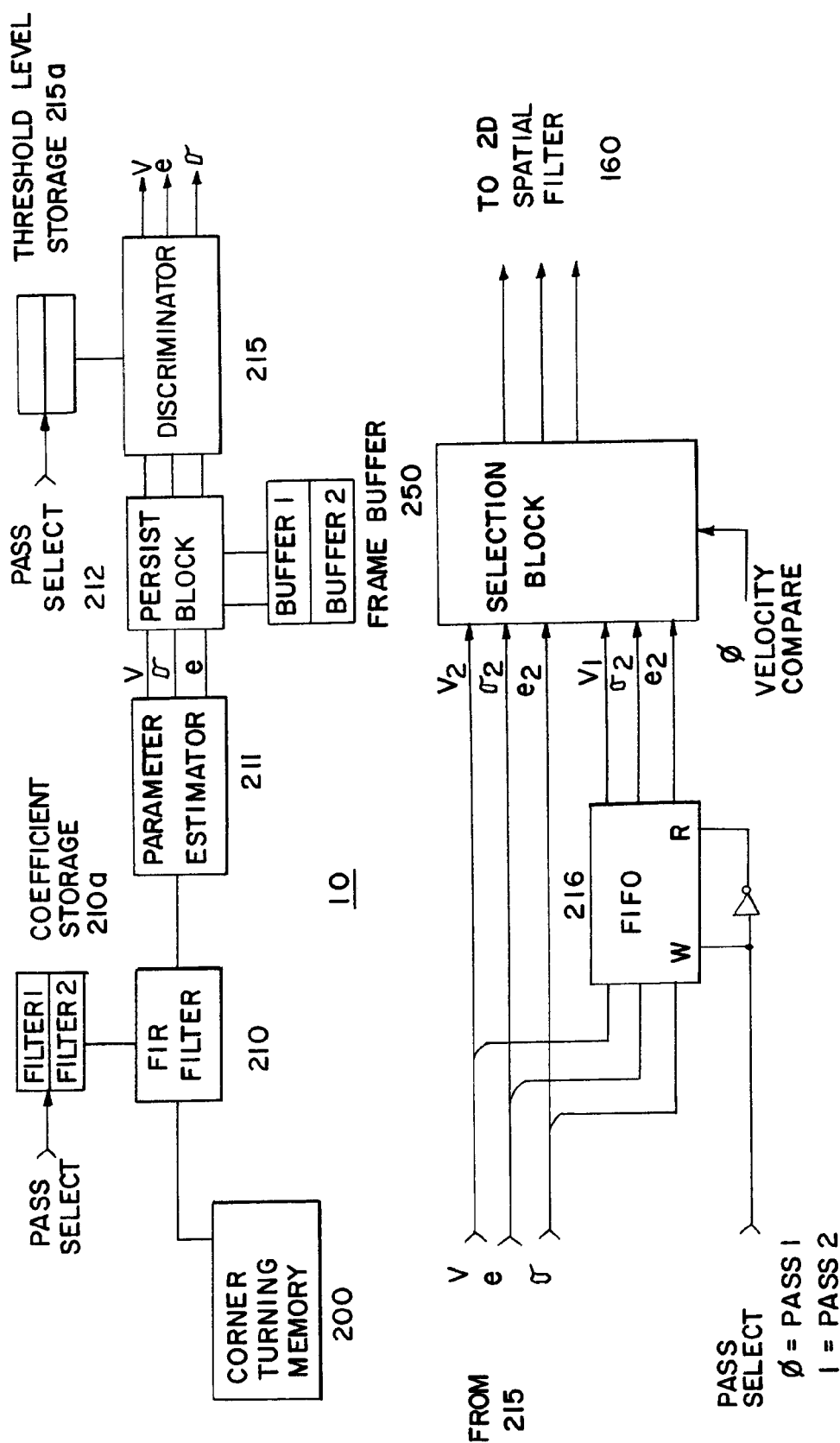

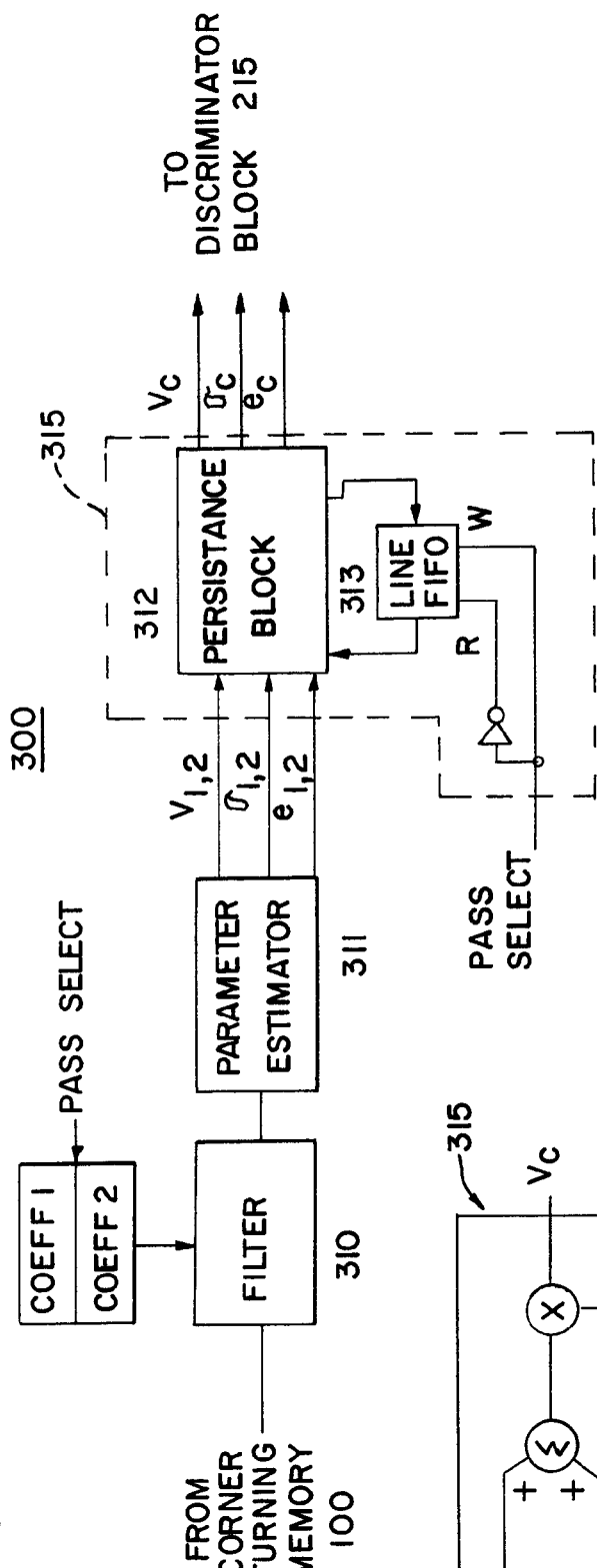
FIG. 4 ENERGY WEIGHTED MULTIPASS COMBINING
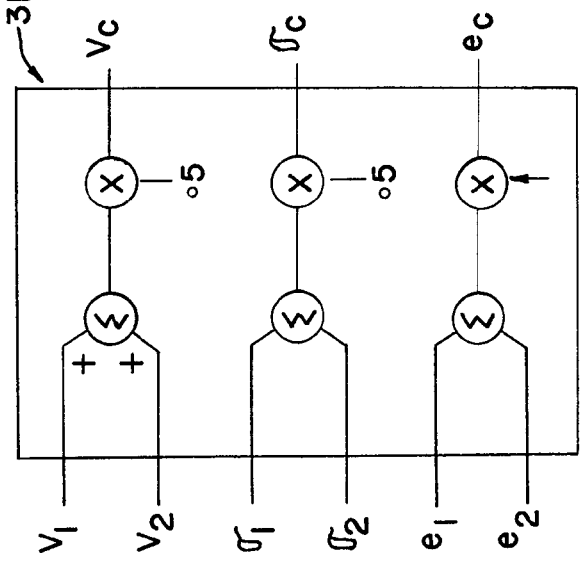
FIG. 5 FILTER BLOCK - SIMPLE ARITHMETIC AVERAGE

MEDICAL DIAGNOSTIC ULTRASOUND SYSTEM AND METHOD FOR IMPROVED FLOW OR MOVEMENT DETECTION WITH MULTIPLE CLUTTER FILTERS

BACKGROUND

This invention relates to a medical diagnostic ultrasound system and method for imaging blood flow or tissue movement. In particular, clutter filtering for flow or movement imaging is provided.

Ultrasound systems image blood flow and tissue movement using correlation or Doppler techniques. The flow or movement is represented by one or more of various estimated parameters, such as energy, velocity and/or variance. Prior to estimation of these parameters, a clutter filter may suppress undesired signals, such as associated with reflections of ultrasonic energy from stationary or slowly moving tissue.

The clutter filter response is typically selected as a compromise between low flow or movement sensitivity, clutter suppression, and the number of taps for the clutter filter. A large number of taps allows filters with a sharper magnitude versus frequency rolloff, more efficiently isolating desired signals from undesired signals (i.e. better differentiation between flow or movement and clutter). The large number of taps allows for better sensitivity to low velocity flow or movement. The large number of taps also allows for filtering with a flat frequency passband, providing more desirable sensitivity over a larger range of velocities.

However, more line firings are required for more taps. A larger number of line may reduce the frame rate for imaging.

U.S. Pat. No. 5,249,578 to Karp et al. teaches processing data with different finite impulse response filters where the different filters are defined as having reversed coefficients. The magnitude versus frequency response of these two filters is the same. By using these two filters, a greater number of independent samples may reduce the variance of velocity estimation.

BRIEF SUMMARY

The present invention is defined by the following claims, and nothing in this section should be taken as a limitation on those claims. By way of introduction, the preferred embodiment described below includes a method and system for flow or movement detection. More than one clutter filter is used. Each clutter filter is optimized differently. Estimates of the flow or movement are generated from the data output by each of the clutter filters. Using selection or combination of the resulting estimates, the best attributes of each filter are used for imaging.

In one aspect, a medical diagnostic ultrasound system for estimating flow or movement is provided. The system includes first and second clutter filters. The first clutter filter is characterized by a magnitude versus frequency response different than the second clutter filter. A combiner is operatively connected to receive first and second estimates. The first and second estimates are responsive to the first and second clutter filters, respectively. The combiner is operable to combine the first and second estimates. In other aspects, the combiner is replaced with a selector. The selector is operable to select one of the first and second estimates.

In another aspect, a medical diagnostic ultrasound method for estimating flow or movement is provided. The method includes the steps of filtering with a first clutter filter and filtering with a second clutter filter where the first clutter filter is characterized by a magnitude versus frequency response different than the second clutter filter. First and second estimates are estimated from data from the first and second clutter filters, respectively. The first and second estimates are combined, or one of the first and second estimates is selected.

Further aspects and advantages of the invention are discussed below in conjunction with the preferred embodiments.

BRIEF DESCRIPTION OF SEVERAL VIEWS OF THE DRAWINGS

FIG. 1 is a block diagram of one embodiment of a medical diagnostic ultrasound system for estimating flow or movement.

FIG. 2 is a block diagram of one embodiment of a selector in the system of FIG. 1.

FIG. 3 is a block diagram of another embodiment of a medical diagnostic ultrasound system for estimating flow or movement.

FIG. 4 is a block diagram of one embodiment of a combiner for use in the system of FIG. 3.

FIG. 5 is a block diagram of one embodiment of a combiner for use in the systems of FIGS. 1 or 3.

DETAILED DESCRIPTION OF THE INVENTION

Figure 6:
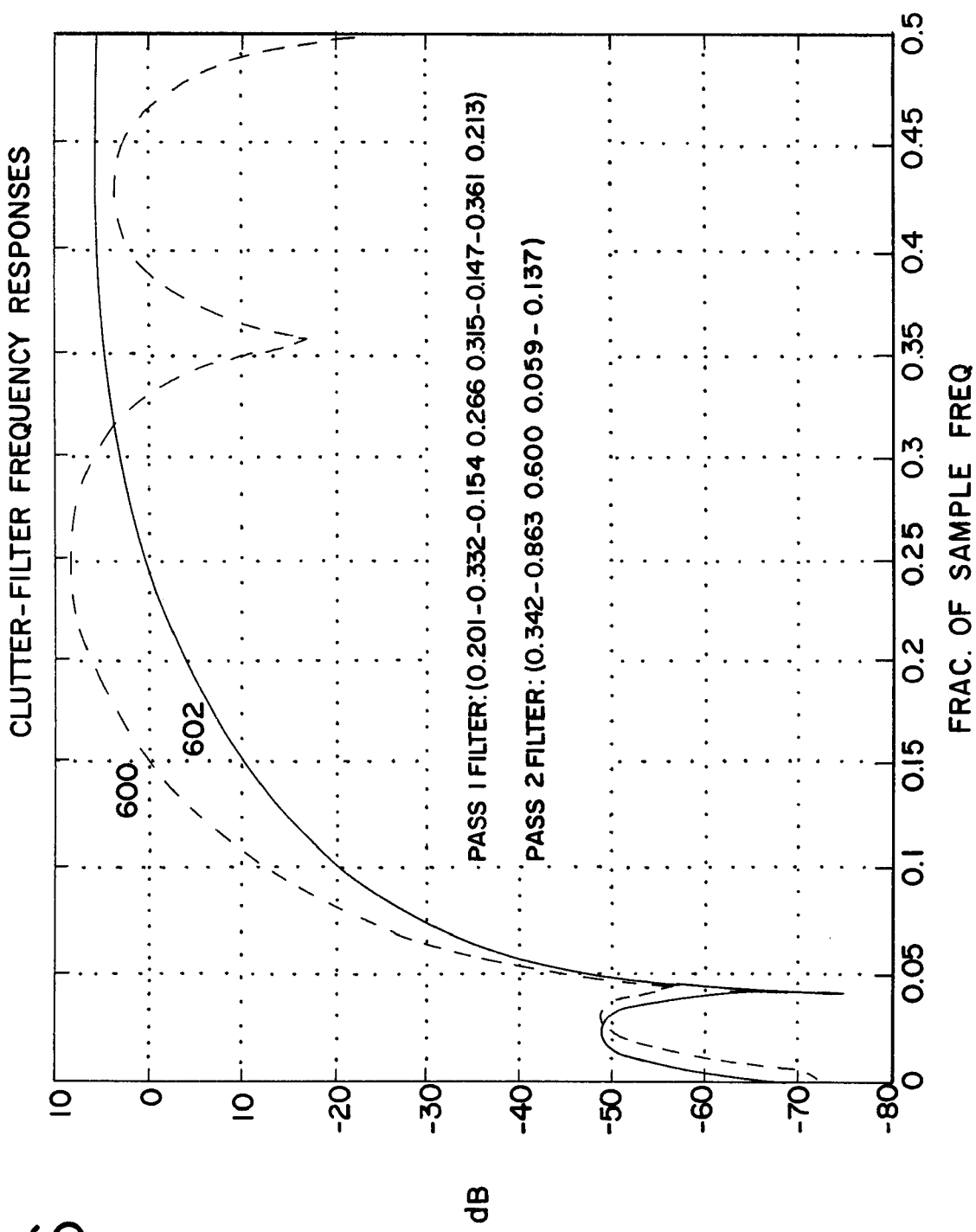
FIG. 6 is a graphical representation of magnitude versus frequency responses of two clutter filters.

The medical ultrasonic diagnostic systems and methods described herein may provide for improved imaging of blood flow or tissue movement. Two clutter filters with different magnitude versus frequency responses filter data prior to estimation. Preferably, the same data is input to both filters. Estimates are generated from the output of each clutter filter. The best estimate is selected or multiple estimates are combined. The selected or combined estimates are used to generate an image with increased low flow or movement sensitivity, increased high flow or movement sensitivity and/or increased frame rate. The systems and methods use separate paths or sequentially use a same path for the clutter filtering.

Referring to FIG. 1, one preferred system for estimating flow or movement is shown at 90. The system 90 includes a corner turning memory 100, two different clutter filtering paths 102 and 104, a selection block 150, a spatial filter 160, a temporal filter 170, a CINE memory 180, a scan converter 190, a color mapping processor 191 and a display 192. More or fewer components may be used. The components may also be placed in a different order for processing. The system 90 may comprise any of various ultrasound systems, such as the 128XP, Aspen or Sequoia ultrasound systems manufactured by Acuson Corporation. Ultrasound systems manufactured by others may also be used.

In operation, the corner turning memory 100 stores data associated with multiple transmissions along a same scan line. The data comprises radio frequency or in-phase and quadrature (I/Q) data. The data is filtered by the clutter filtering paths 102 and 104. The filtered data is used to estimate parameters representing flow or movement, such as energy, velocity and/or variance, at each spatial location or range along the scan line for a given time. Each clutter filtering path 102 and 104 generates separate estimates for the same spatial locations. The selection block 150 selects estimates from one of the two clutter filtering paths 102 and 104. The selected estimates are spatially filtered by spatial filter 160 and temporally filtered by the temporal filter 170. The filtered estimates are stored in the CINE memory for later review. The scan converter 190 re-formats the estimates for display. The color mapping processor 191 determines colors for display to represent the estimates and combines with any B-mode images. Based on the colors, an image representing flow or movement is generated on the display Each clutter filtering path 102, 104 includes a clutter filter 110, 120, an estimator 111, 121, and a discriminator 115, 125. In alternative embodiments, the discriminator 115, 125 is not provided. Additional components may be included within the clutter filtering paths 102, 104, including components represented in other portions of the system 90 (e.g. temporal or spatial filters 160 or 170). In an alternative embodiment, one clutter filter path 102 has different components than the other clutter filter path 104.

The clutter filters 110 and 120 preferably comprise finite impulse response filters (FIR), infinite impulse response filters (IIR) or combinations thereof. The clutter filters 110 and 120 are either static or programmable. In one embodiment, the clutter filters 110 and 120 comprise digital signal processors. Other known or yet to be developed clutter filters may be used, such as processors or dedicated hardware. The same or different type of hardware may be used for each of the clutter filters 110 and 120. Preferably, the clutter filters 110 and 120 comprise programmable FIR filters.

The clutter filters 110 and 120 have a different magnitude versus frequency response. For example, different cut-off frequencies are used, different rolloffs are used (e.g. sharper or more gradual rolloff for one clutter filter), and/or different passband shapes are used (e.g. more flat or different magnitude versus frequency notches).

The clutter filters 110, 120, in particular the coefficients and the number of taps defining the magnitude versus frequency response, are selected as a function of the imaging application and experimentation. Referring to FIG. 6, the frequency response for two preferred clutter filters 110,120 is shown at 600 and 602, respectively. The log magnitude response 600, 602 of each clutter filter 110, 120 is shown. The sampling frequency is 1 divided by the pulse repetition interval (PRI). These two magnitude versus frequency responses 600 and 602 are preferred for each path 102 and 104 (FIG. 1), respectively, for general imaging applications, such as kidney or liver imaging with a center frequency from 2–5 MHz and PRIs ranging from 320 to 2400 microseconds. Other center frequencies and PRIs with the same or different clutter filters 110, 120 may be used.

One magnitude versus frequency response 600 is responsive to an 8 tap clutter filter with the filter coefficients of [0.201, −0.332, −0.154, 0.266, 0.315, −0.147, −0.361, 0.213]. The other magnitude versus frequency response is responsive to a 5 tap clutter filter with the filter coefficients of [0.342, −0.863, 0.600, 0.059, −0.137]. More or fewer taps and/or different coefficients may be used.

Both magnitude versus frequency responses have similar stopband performance, such as in the range of frequencies below about 0.05 times that of the sample frequency (1/PRI). One magnitude versus frequency response 600 has a higher magnitude below about 0.31 than the other magnitude versus frequency response 602. Above this frequency, the magnitude of the one magnitude versus frequency response 600 is degraded since the coefficients and number of taps have been selected to obtain a higher response at the lower frequencies with a sharper rolloff. The clutter filter 110 associated with the one magnitude versus frequency response 600 provides data for better low flow or movement velocity sensitivity. The clutter filter 120 associated with the other magnitude versus frequency response 602 provides data for better higher velocity estimation. This clutter filter 120 produces a stronger output for frequencies above 0.31 but has a more gradual rolloff. By combining or selecting from the parameters estimated from both clutter filters 110, 120, better overall performance for imaging flow or movement is provided.

None, one or more of the clutter filters 110, 120 decimate to increase the low velocity sensitivity. The resulting velocity estimates are scaled by dividing by the decimation factor before selection or combination. In one embodiment, one clutter filter 110 decimates and the other clutter filter 120 outputs data at the same rate as the data is input. The parameters estimated from data output by the decimating clutter filter 110 are combined with the parameters estimated from the data output by the non decimating clutter filter 120. This embodiment provides better overall sensitivity over a wider passband.

In an alternative or addition to the various embodiments above, one or more of the clutter filters 110, 120 comprise complex clutter filters. For example, a complex filter has a passband substantially in positive frequencies while rejecting low frequency clutter and negative frequencies. The other clutter filter 120 has a passband characterized as a complex conjugate of the first filter. The complex conjugate filter has a passband in negative frequencies and rejects positive frequencies. Other complex filters and passbands may be used.

Referring to FIG. 1, the output from each of the clutter filters 110, 120 is provided to the two estimators 111, 121, respectively. The estimators 111, 121 comprise digital signal processors, general processors, dedicated hardware, other known or yet to be developed devices for estimating flow or movement parameters, and combinations thereof. The estimators 111, 121 estimate a set of parameters for each spatial location. In one embodiment, the set of parameters includes velocity, variance and energy. More, fewer or different parameters may be estimated. The parameters are obtained from auto-correlation processing, cross correlation processing, Doppler processing or other similar methods. The parameters are estimated as auto-correlation values, R0 and complex R1 or other parameters related to Doppler energy, velocity, and variance.

The sets of estimates are output to the discriminators 115, 125. The discriminators 115, 125 comprise digital signal processors, general processors, dedicated hardware, RAM look-up tables or other devices for applying a threshold to the estimates. The discriminators 115, 125 set all or a subset of the estimates to zero where the energy estimate is below an energy threshold or the velocity estimate is below a velocity threshold. The thresholds are selected to reject noise and low level signals for energy estimates and to reject low velocity clutter from tissue motion for velocity estimates. The levels of these thresholds is set independently for each clutter filter path 102, 104. Preferably, the thresholds applied by each discriminator 115, 125 are the same. Different thresholds to reject different signals may be used, such as different thresholds for flow than for tissue movement. The velocity threshold levels are determined experimentally and typically range from velocities with Doppler frequencies of 0.05 to 0.20 times the sample frequency, depending on the clinical situation, operating frequency, and PRI. The energy threshold typically ranges from 6 to 12 dB above the system noise floor. In alternative embodiments, a threshold is not applied to one or both of energy and velocity estimates prior to combination. In yet other alternative embodiments, one type of parameter is used to set estimate values for another type of parameter, such as velocity thresholds for energy estimates.

The sets of estimates output by the discriminators 115, 125 are input to the selector 150. The selector 150 comprises a digital signal processor, a general processor, dedicated hardware, a RAM look-up table or other devices for comparing and selecting estimates. Preferably, the selector 150 selects the set of estimates for imaging that includes the highest velocity magnitude. Other parameters may be used for the selection, such as energy estimates. In alternative embodiments, each type of parameter or a subset is selected independently. For example, velocity is selected from one clutter filter path 102 and energy is selected from the other clutter filter path 104 for representing the same spatial location. In this example, variance is selected either independently or as a function of the energy or the velocity selection.

Referring to FIG. 2, a block diagram of a preferred structure for the selector 150 is shown. The selector 150 comprises absolute value blocks 151, 152, comparitors 153, 154, a comparison select multiplexer 155 and a estimate selection multiplexer 156. Preferably, the selector 150 comprises a single field programmable gate array. In alternative embodiments, these components comprise separate dedicated hardware or one or more of the components is implemented with a processor. For example, the absolute value blocks 151, 152 and the comparitors 153, 154 are implemented with a single processor.

The absolute value blocks 151, 152 convert signed velocity estimates to velocity magnitude estimates for selection determination.

One comparitor 153 compares the velocity magnitude from the two different clutter filter paths 102, 104 (FIG. 1). Another comparitor 154 compares the energy from the two different clutter filter paths 102, 104. The set of estimates associated with the highest velocity magnitude and the highest energy is identified by the comparitors 153, 154, respectively. The lowest values or values closest to a threshold may also or alternatively be used to identify the set of parameters. In alternative embodiments, one comparitor 153, 154 is provided for either of velocity, energy or variance comparison. In yet other alternative embodiments, different parameters are compared, such as variance.

In the preferred embodiment, the velocity magnitude and energy comparison used for selecting estimates is selectable. Variance comparison may also be provided. The multiplexer 155 receives control input to select velocity magnitude or energy comparison. In response to the control input, the comparison selection multiplexer 155 outputs the identification of the set of parameters from the appropriate comparitor 153, 154.

The estimate selection multiplexer 156 receives the identification information as a control input. In response to the comparison control input information, the estimate selection multiplexer 156 passes one set of estimates for further image processing. For example, velocity magnitude comparison is selected for estimate selection. The comparitor 153 identifies the clutter filter path 102, 104 corresponding to the set of estimates with the highest velocity magnitude. The comparison selection multiplexer 155 passes the identification from the velocity comparitor 153. The estimate selection multiplexer 156 passes the set of estimates corresponding to the identified clutter filter path 102, 104.

In an alternative embodiment, a RAM look-up table is used for selection of the set of estimates. The look-up table is responsive to the parameters discussed above, such as velocity or energy, or multiple parameters. For example, the parameter set with the highest energy is selected unless the difference between the energies in each set is less than a threshold. If the energies are close, then the set of estimates corresponding to the lowest variance is selected. Other structures and comparison combinations may be used, including independent comparison of velocity, variance or energy or dependent comparison of any combination of velocity, variance and/or energy.

FIG. 1 represents a system 90 for selecting from two parallel clutter filter paths 102, 104. Referring to FIG. 3, an alternative system 190 that uses sequential processing to obtain the sets of estimates using clutter filters with different magnitude versus frequency responses is shown. The system 190 comprises a clutter filter 210, a coefficient storage 210a, an estimator 211, a persistence filter 212, a discriminator 215, a threshold level storage 215a, a memory 216, and a selector 250.

The corner turning memory 200 provides data to the single clutter filter 210. The clutter filter preferably comprises a programmable FIR filter, but other programmable filters discussed above may be used. The coefficient storage 210a contains at least two different coefficient sets, such as the coefficients shown in FIG. 6. The coefficient set in use is selected depending on the sequential data pass-pass1 (the first pass) or pass2 (the second pass). On the first pass, data for one acoustic line of parameter estimates is read out of the corner turning memory 200 and processed by the clutter filter 210 programmed with coefficient set 1. The flow parameters velocity, variance, and energy are estimated by estimator 211.

The optional persistence filter 212 comprises a digital signal processor, a general processor or dedicated hardware including a memory for buffering data. The persistence filter 212 optionally performs frame based temporal persistence. Independent frame storage for each processing pass for each set of parameter estimates is provided for persisting. Each new set of estimates is persisted with previous sets of estimates from the same pass (e.g., pass 1 or pass 2).

The estimates are passed to the discriminator 215 where a lower energy threshold and/or a velocity threshold are applied to the estimates. The levels of these thresholds is set independently for each processing pass by downloading different thresholds from the threshold storage block 215a. Preferably, the same thresholds are used for each pass. Other thresholds, such as discussed above, may be used.

The estimates from the first pass are stored in the memory 216. The memory 216 preferably comprises a line FIFO buffer, but may comprise a RAM, buffer, or other memory devices.

The process is repeated for the second pass. Preferably, the same data is output by the corner turning memory 200. A subset of data may be output to speed processing where some data is not needed due to the characteristics (e.g., number of taps) of the clutter filter. The clutter filter 210 is programmed with different coefficients from the memory 210a for the second pass. The second set of estimates is obtained, persisted, thresholded, and input to the selector 250 with the first set of estimates stored in the memory 216.

As discussed above, estimates are selected for further processing and imaging by the selector 250. The selected estimates are output for further processing as discussed above for FIG. 1. The clutter filter coefficients, the thresholds, the persistence filter characteristics, the pass selector and any other controllable components are controlled by a controller.

In another embodiment, the sets of estimates are combined for imaging. Referring to FIG. 4, one embodiment for combining the sets of estimates using sequential clutter filtering is shown at 300. Combining the sets of estimates may also be used with the parallel clutter filter paths 102, 104 of FIG. 1. The system 300 includes a clutter filter and associated coefficient memory 310, an estimator 311 and a combiner 315. The clutter filter and associated coefficient memory 310 and the estimator 311 operate as described above.

The combiner 315 comprises a persistence filter 312 and memory 313. In alternative embodiments, the combiner 315 comprises a RAM look-up table, a digital signal processor, a general processor, dedicated hardware or other devices for combining estimates. The persistence filter 312 passes the estimates to the memory 313 for the first pass. For the second pass, the persistence filter 312 combines the sets of estimates, one set from the memory 313 and the other set from the estimator 311.

Any of various combination functions may be used, such as averaging, weighted averaging, linear combinations, and non-linear combinations. Different functions may be used for different types of estimates, such as one function for combining velocity estimates and a different function for combining energy estimates. Either energy or the log of the energy may be combined. In one embodiment, energy weighted combinations of velocity estimates is performed as disclosed in U.S. Pat. Nos. 5,609,155 and 5,860,930, the disclosures of which are incorporated herein by reference. For example, the velocity output by the combiner 315 is represented as (E1*V1+E2*V2)/(E1+E2), where E1 and V1 are the energy and velocity of a first set and E2 and V2 are the energy and velocity of a second set.

Referring to FIG. 5, an alternative embodiment of the combiner 315 is shown. The combiner 315 comprises a filter, digital signal processor, general processor, summers and multipliers, or other devices for averaging data. The combiner 315 sums the sets of estimates. In particular, the estimates for each type of estimate are summed together. The total for each type of estimate is multiplied by ½. The resulting averages are output for further processing and imaging. Preferably, the combination is performed after discrimination.

Combining the estimates results in estimates optimized as a function of the attributes of two different clutter filters. The advantages of each individual clutter filter are provided without the disadvantages, such as degraded frame rate, of a single filter. If complex clutter filters are used with a combiner 315, the multiple complex clutter filter attributes produce combined parameter estimates which have a better signal to noise ratio over a wider bandwidth than the filters by themselves or by a real filter with a passband that is substantially similar to the combined passbands of the complex filters.

In one embodiment, one or more clutter filters comprise adaptive clutter filters. For example, the adaptive clutter filters disclosed in U.S. Pat. Nos. 5,544,659 and 5,664,575, the disclosures of which are incorporated herein by reference, are used. Other adaptive clutter filters may be used, such as where the coefficients and/or number of taps are selected as a function of ultrasound data. Where both clutter filters are adaptive, different functions for adaptation may be used, resulting in different magnitude versus frequency responses.

In further embodiments, more than two clutter filter paths or passes with a corresponding more than two different magnitude versus frequency responses are provided. For example, a collection of narrowband clutter filters boosts overall sensitivity over a greater range of desired Doppler frequencies than a single filter or two filters.

While the invention has been described above by reference to various embodiments, it will be understood that many changes and modifications can be made without departing from the scope of the invention. For example, other known or yet to be developed clutter filters, estimators, combiners, and selectors may be used.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A medical diagnostic ultrasound system for estimating flow or movement, the system comprising:
   first and second clutter filters, the first clutter filter characterized by a magnitude versus frequency response different than the second clutter filter;
   a combiner operatively connected to receive first and second estimates, the first and second estimates being responsive to the first and second clutter filters, respectively, the combiner operable to combine the first and second estimates.

2. The system of claim 1 wherein the first and second estimates comprise estimates selected from a group of velocity, energy, variance and combinations thereof.

3. The system of claim 1 wherein same data is input to the first and second clutter filters.

4. The system of claim 1 wherein the first and second clutter filters comprise a same programmable filter.

5. The system of claim 1 further comprising a memory, wherein the first estimate is stored in the memory while the second estimate is created.

6. The system of claim 1 wherein the combiner averages the first and second estimates.

7. The system of claim 1 wherein the first and second estimates comprise velocity estimates and the combiner is operable to combine the first and second estimates weighted by energy estimates.

8. The system of claim 1 wherein the first clutter filter has a sharper magnitude versus frequency response rolloff than the second clutter filter.

9. The system of claim 1 wherein the first clutter filter comprises a programmable finite impulse response filter.

10. The system of claim 1 wherein the first and second clutter filters comprise complex filters.

11. The system of claim 1 wherein the combiner comprises a look-up-table memory.

12. The system of claim 1 wherein the first clutter filter is responsive to a greater number of coefficients than the second clutter filter.

13. A medical diagnostic ultrasound system for estimating flow or movement, the system comprising:
   first and second clutter filters, the first clutter filter characterized by a magnitude versus frequency response different than the second clutter filter;
   a selector operatively connected to receive first and second estimates, the first and second estimates a function of the first and second clutter filters, respectively, the selector operable to select one of the first and second estimates.

14. The system of claim 13 wherein the selector comprises a look-up-table memory operable to select a first set of parameters associated with a highest energy where the energy associated with a second set of parameters is less than the highest energy by a threshold amount and to otherwise select one of the first and second sets of parameters as a function of variance.

15. The system of claim 13 wherein the selector comprises:

a comparitor operatively connected to receive the first and second estimates;

a multiplexer operative to pass selected estimates in response to the comparitor.

16. The system of claim 13 wherein the first and second estimates comprise velocity estimates, the selector operative to select one of the first and second estimates, the selected one having a highest velocity magnitude.

17. The system of claim 13 wherein the same data is input to the first and second clutter filters.

18. The system of claim 13 wherein the first and second clutter filters comprise a same programmable filter.

19. The system of claim 13 further comprising a memory, wherein the first estimate is stored in the memory while the second estimate is created.

20. The system of claim 13 wherein the first clutter filter has a sharper magnitude versus frequency response rolloff than the second clutter filter.

21. The system of claim 13 wherein the first clutter filter comprises a programmable finite impulse response filter.

22. The system of claim 13 wherein the first and second clutter filters comprise complex filters.

23. The system of claim 13 wherein the selector comprises a look-up-table memory.

24. The system of claim 13 wherein the first clutter filter is responsive to a greater number of coefficients than the second clutter filter.

25. A medical diagnostic ultrasound method for estimating flow or movement, the method comprising the steps of:

(a) filtering with a first clutter filter;

(b) filtering with a second clutter filter, the first clutter filter characterized by a magnitude versus frequency response different than the second clutter filter;

(c) estimating first and second estimates responsive to steps (a) and (b), respectively;

(d) selecting one of the first and second estimates.

26. The method of claim 25 wherein step (d) comprises selecting a firs set of parameters associated with a highest energy where the energy associated with a second set of parameters is less than the highest energy by a threshold amount and to otherwise select one of the first and second sets of parameters as a function of variance.

27. The method of claim 25 wherein step (d) comprises:

(d1) comparing the first and second estimates;

(d2) passing one of the first and second estimates in response to step (d1).

28. The method of claim 25 wherein step (c) comprises estimating first and second velocities and step (d) comprises selecting the estimate with the highest velocity magnitude.

29. The method of claim 25 further comprising:

(e) inputting same data to the first and second clutter filters for steps (a) and (b).

30. The method of claim 25 wherein the first and second clutter filters comprise a same programmable filter and further comprising:

(e) programming the first clutter filter; and (f) programming the second clutter filter.

31. The method of claim 30 further comprising:

(g) storing the first estimate in a memory while step (b) is performed.

32. The method of claim 25 wherein step (a) comprises filtering where the first clutter filter has a sharper magnitude versus frequency response rolloff than the second clutter filter.

33. The method of claim 25 wherein step (a) comprises filtering with the first clutter filter comprising a programmable finite impulse response filter.

34. The method of claim 25 wherein step (d) comprises inputting the first and second estimates into a look-up-table memory.

35. The method of claim 25 wherein the first clutter filter is responsive to a greater number of coefficients than the second clutter filter.

36. A medical diagnostic ultrasound method for estimating flow or movement, the method comprising the steps of:

(a) filtering with a first clutter filter;

(b) filtering with a second clutter filter, the first clutter filter characterized by a magnitude frequency response different than the second clutter filter;

(c) estimating first and second estimates responsive to steps (a) and (b), respectively;

(d) combining the first and second estimates.

37. The method of claim 36 wherein step (c) comprises estimating first and second velocities.

38. The method of claim 36 further comprising:

(e) inputting same data to the first and second clutter filters for steps (a) and (b).

39. The method of claim 36 wherein the first and second clutter filters comprise a same programmable filter and further comprising:

(e) programming the first clutter filter; and (f) programming the second clutter filter.

40. The method of claim 39 further comprising:

(g) storing the first estimate in a memory while step (b) is performed.

41. The method of claim 36 wherein step (a) comprises filtering where the first clutter filter has a magnitude versus frequency sharper rolloff than the second clutter filter.

42. The method of claim 36 wherein step (a) comprises filtering with the first clutter filter comprising a programmable finite impulse response filter.

43. The method of claim 36 wherein step (d) comprises inputting the first and second estimates into a look-up-table memory.

44. The method of claim 36 wherein the first clutter filter is responsive to a greater number of coefficients than the second clutter filter.

45. The method of claim 36 wherein step (d) comprises averaging the first and second estimates.

46. The method of claim 36 wherein step (d) comprises:

(d1) weighting the first and second estimates; and (d2) averaging the weighted first and second estimates.

47. The system of claim 1 further comprising at least a third clutter filter.

48. The system of claim 13 further comprising at least a third clutter filter.

49. The system of claim 1 wherein a subset of data input to the first clutter filter is input to the second clutter filter.

50. The system of claim 1 wherein the first clutter filter comprises an infinite impulse response filter.

51. The system of claim 1 wherein the first clutter filter comprises an adaptive filter.

52. The system of claim 13 wherein a subset of data input to the first clutter filter is input to the second clutter filter.

53. The system of claim 13 wherein the first clutter filter comprises an infinite impulse response filter.

54. The system of claim 13 wherein the first clutter filter comprises an adaptive filter.

55. The method of claim 25 further comprising (e) inputting a subset of data input to the first clutter filter into the second clutter filter.

56. The method of claim 25 wherein steps (a) comprises filtering with the first clutter filter comprising an infinite impulse response filter.

57. The method of claim 25 wherein step (a) comprises adaptively filtering.

58. The method of claim 36 further comprising (e) inputting a subset of data input to the first clutter filter into the second clutter filter.

59. The method of claim 36 wherein steps (a) comprises filtering with the first clutter filter comprising an infinite impulse response filter.

60. The method of claim 36 wherein step (a) comprises adaptively filtering.

\* \* \* \* \*